(12) United States Patent
Hashim (10) Patent No.: US 12,035,448 B2
(45) Date of Patent: Jul. 9, 2024

(54) DIELECTRIC HEATING OF THREE-DIMENSIONAL CARBON NANOSTRUCTURED POROUS FOAMS AS A HEAT EXCHANGER FOR VOLUMETRIC HEATING OF FLOWING FLUIDS

(71) Applicant: Daniel Paul Hashim, La Jolla, CA (US)

(72) Inventor: Daniel Paul Hashim, La Jolla, CA (US)

( * ) Notice: Subject to any disclaimer, the term of this patent is extended or adjusted under 35 U.S.C. 154(b) by 966 days.

(21) Appl. No.: 16/463,733

(22) PCT Filed: Nov. 23, 2016

(86) PCT No.: PCT/US2016/063705
§ 371 (c)(1),
(2) Date: May 23, 2019

(87) PCT Pub. No.: WO2017/091790
PCT Pub. Date: Jun. 1, 2017

(65) Prior Publication Data
US 2019/0387587 A1 Dec. 19, 2019

Related U.S. Application Data

(60) Provisional application No. 62/258,980, filed on Nov. 23, 2015.

(51) Int. Cl.
*H05B 6/80* (2006.01)
*C07C 7/00* (2006.01)
(Continued)

(52) U.S. Cl.
CPC ............. *H05B 6/802* (2013.01); *C07C 7/005* (2013.01); *C07C 7/12* (2013.01); *C10G 25/003* (2013.01);
(Continued)

(58) Field of Classification Search
CPC ........... H05B 6/802; C07C 7/005; C07C 7/12; C10G 25/003; C10G 32/02;
(Continued)

(56) References Cited

U.S. PATENT DOCUMENTS 3,922,334 A * 11/1975 Marek ........................ C08J 9/42
427/244
3,927,186 A * 12/1975 Vinton .................... C04B 35/83
423/447.7

(Continued)

*Primary Examiner* — Raheena R Malik
(74) *Attorney, Agent, or Firm* — David S. Bradin; Maynard Nexsen PC (57) ABSTRACT

A system and method are described for heating a substance (i.e., liquid, gas, and/or an absorbed solid) using a carbon nanostructured porous foam as a heat transfer material and an electronic heat source. In some embodiments, the heat source may be a microwave volumetric heating (MVH) system. The method for heating, vaporizing, or decomposing any of the desired substance may involve filtering or continuously flowing the substance through the carbon nanostructured porous foam heat transfer material, resulting in physical confinement or absorption of the substance, and subjecting the carbon nanostructure porous foam heat transfer material to sufficient electronic radiation.

21 Claims, 5 Drawing Sheets

(51) Int. Cl.
*C07C 7/12* (2006.01)
*C10G 25/00* (2006.01)
*C10G 32/02* (2006.01)
*C10L 5/04* (2006.01)
*C10L 5/40* (2006.01)
*C10L 9/08* (2006.01)
*F28F 13/00* (2006.01)
*F28F 21/02* (2006.01)
*H05B 6/60* (2006.01)

(52) U.S. Cl.
CPC ............... *C10G 32/02* (2013.01); *C10L 5/04* (2013.01); *C10L 5/40* (2013.01); *C10L 9/08* (2013.01); *F28F 13/003* (2013.01); *F28F 21/02* (2013.01); *H05B 6/60* (2013.01); *C10G 2300/207* (2013.01); *C10L 2290/36* (2013.01); *C10L 2290/542* (2013.01)

(58) Field of Classification Search
CPC ....... C10G 2300/207; C10L 5/04; C10L 5/40; C10L 9/08; C10L 2290/36; F28F 13/003; F28F 21/02
USPC .......................................................... 219/678
See application file for complete search history.

(56) References Cited

U.S. PATENT DOCUMENTS

| | | | | |
|---|---|---|---|---|
| 4,019,021 A * | 4/1977 | Schladitz | ............... | H05B 3/141 |
| | | | | 219/601 |
| 4,067,956 A * | 1/1978 | Franklin | ................. | H01M 4/64 |
| | | | | 428/408 |
| 4,220,846 A * | 9/1980 | Rice | ........................ | H01C 17/20 |
| | | | | 252/502 |
| 4,310,747 A * | 1/1982 | Rice | ...................... | H05B 3/145 |
| | | | | 338/225 |
| 5,764,850 A * | 6/1998 | Olstad | ..................... | F23D 14/66 |
| | | | | 219/544 |
| 8,046,956 B1 * | 11/2011 | Hohmann, Jr. | ........ | E04B 1/7046 |
| | | | | 52/302.1 |
| 9,338,828 B2 * | 5/2016 | McGuffey | ................ | H05B 3/16 |
| 9,459,024 B2 * | 10/2016 | Ghasemi | ................ | F24S 90/00 |
| 9,581,282 B1 * | 2/2017 | Ward | ...................... | B32B 9/007 |
| 9,657,723 B1 * | 5/2017 | Iyer | ............................ | F22B 31/0007 |
| 10,234,172 B2 * | 3/2019 | Ni | ............................. | F24S 90/00 |
| 2012/0238021 A1 * | 9/2012 | Hashim | ................ | B01J 20/0248 |
| | | | | 423/276 |
| 2012/0285660 A1 * | 11/2012 | Poltorak | ............. | H05K 7/20509 |
| | | | | 165/104.11 |
| 2014/0034282 A1 * | 2/2014 | Kawamura | ......... | H01L 23/3736 |
| | | | | 165/185 |
| 2014/0124186 A1 * | 5/2014 | Suwa | .................... | F28F 13/185 |
| | | | | 977/932 |
| 2015/0219410 A1 * | 8/2015 | Lin | ......................... | F28F 13/18 |
| | | | | 165/133 |
| 2015/0263339 A1 * | 9/2015 | Kouzu | .................. | H01M 4/131 |
| | | | | 429/231.4 |
| 2016/0351918 A1 * | 12/2016 | Yun | ....................... | C01B 32/174 |

\* cited by examiner

| Carbon material | $\tan\delta = \varepsilon''/\varepsilon'$ |
| --- | --- |
| Coal | 0.02-0.08 |
| Carbon foam | 0.05-0.20 |
| Charcoal | 0.11-0.29 |
| Carbon black | 0.35-0.83 |
| Activated carbon | 0.57-0.80 |
| Activated carbon[a] | 0.22-2.95 |
| Carbon nanotube | 0.25-1.14 |
| CSi nanofibres | 0.58-1.00 |

FIGURE 4

| Reaction |
|---|
| $C + 2NO \rightarrow CO_2 + N_2$ |
| $C + NO \rightarrow CO + 1/2 N_2$ |
| $C + SO_2 \rightarrow CO_2 + S$ |
| $2C + SO_2 \rightarrow 2CO + S$ |
| $C + CO_2 \leftrightarrow 2CO$ |
| $CH_4 \rightarrow C + 2H_2$ |
| $CH_4 + CO_2 \leftrightarrow 2CO + 2H_2$ |

FIGURE 5

DIELECTRIC HEATING OF THREE-DIMENSIONAL CARBON NANOSTRUCTURED POROUS FOAMS AS A HEAT EXCHANGER FOR VOLUMETRIC HEATING OF FLOWING FLUIDS

CROSS REFERENCE TO RELATED APPLICATION

This application is a 35 U.S.C. § 371 U.S. national phase entry of International Application. PCT/US2016/063705 having an international filing date of Nov. 23, 2016, the contents of which are incorporated herein by reference in their entirety for all purposes.

TECHNICAL FIELD

Embodiments described herein pertain generally to a system and method for absorbing or confining a desired material or substance (i.e., a solid, liquid, or gas) in a dielectric nanostructured porous carbon foam and using an electronic heat source (e.g., a microwave volumetric heating system) to alter the physical or chemical state (e.g. heat, evaporate, vaporize, distill, refine, perform pyrolysis reaction (pyrolyze), chemically "crack" molecules and/or decompose) of the substance.

DETAILED DESCRIPTION

Herein describes a system and method for providing an advanced means to rapidly and efficiently transfer heat to a substance resulting in a selectable physical or chemical transformation, depending upon the desired result.

Figure 1:
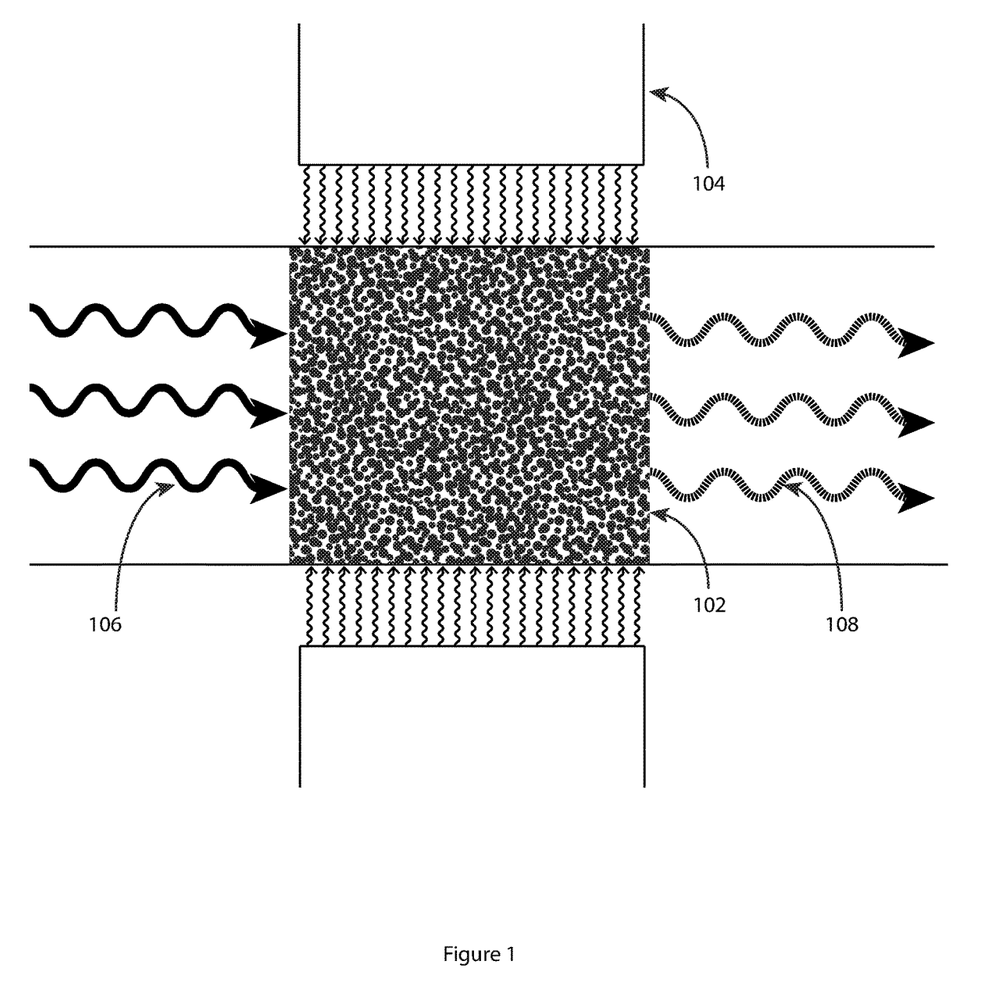
FIG. 1: illustrates a three-dimensional carbon nanostructured porous foam (102) exposed to an electronic energy source (104). A substance (106) (i.e. liquid, gases, and/or solids) may be flowing through the nanostructured porous carbon foam or stagnant within the carbon foam. Within the nanostructured porous carbon foam exposed to the electronic energy there is an increase in temperature. The nanostructured porous carbon foam acts as a heat transfer material to the substance 106.

A three-dimensional carbon nanostructured porous foam 102 may be comprised of nanotubes, graphene, graphite microtubes or microfibers, or any combination thereof. The three-dimensional carbon nanostructured porous foam 102 may be micro-scaled or macro-scaled. Examples of potential structures may be found in the aforementioned incorporated by reference patent application entitled, "METHOD OF SYNTHESIZING THREE-DIMENSIONAL HETEROATOM-DOPED CARBON NANOTUBE MACROMATERIALS AND COMPOSITIONS THEREOF", to Hashim. The three-dimensional carbon nanostructured porous foam 102 may contain a plurality of pores allowing a substance (i.e., solid, liquid, and/or gas) to come into contact with or close proximity to the carbon nanostructures. The three-dimensional carbon nanostructured porous foam 102 may be contained in a box, tube, pipe or unit with any geometrical shape or dimensions with continuous fluid flowing through it or static fluid held therein. In one embodiment, the three-dimensional carbon nanostructured porous foam 102 may possess nano-, micro-, meso-, macro-porosity or any combination thereof. Whereas the pore sizes can range from 1 nm to 500 μm. In one embodiment, the three-dimensional carbon nanostructured porous foam 102 may have a porosity greater than 50 percent and can be up to 99.99% porous. In one embodiment, the three-dimensional carbon nanostructured porous foam 102 may have a density less than 1 mg/cc and can be up to 1000 mg/cc.

In one embodiment, the three-dimensional carbon nanostructured porous foam 102 may become saturated with a substance element 106 (i.e. solid, liquid and/or gas). The three-dimensional carbon nanostructured porous foam 102 may absorb the substance element 106 and evolve into a composite structure, similar to a sponge. The three-dimensional carbon nanostructured porous foam 102 may also allow the substance element 106 to flow through the rigid three-dimensional carbon nanostructured porous foam 102 structure. It may also be possible for the substance element to flow into the three-dimensional carbon nanostructured porous foam 102 and persist as a stagnant substance element 106. Each one of the plurality of pores has a relatively high surface-area which is used to increase the area of thermal/mechanical operative contact, coupling the substance element 106 to the three-dimensional carbon nanostructured porous foam 102.

In one embodiment, the three-dimensional carbon nanostructured porous foam 102 may be exposed to electromagnetic radiation or an electronic energy source 104. In one application the electromagnetic radiation or electronic energy source 104 is equivalent to microwaves via a microwave energy source. It may be possible for the three-dimensional carbon nanostructured porous foam 102 to readily absorb the energy radiated by the electromagnetic energy source 104 and therefore act as a dielectric material by converting the absorbed energy into heat. The heat may be transferred to the absorbed, flowing or stagnant substance element 106 within the open pore structure of the three-dimensional carbon nanostructured porous foam 102. The plurality of pores in the three-dimensional carbon nanostructured porous foam 102 framework may act as a porous high surface-area heating element or heat sink. The heat absorbed by the substance element 106 may result in an increase in internal temperature. The temperature increase may be great enough to heat, evaporate, vaporize, distill, refine, perform pyrolysis reaction (pyrolyze), chemically "crack" molecules and/or decompose the substance element 106, identified as element 108.

In one embodiment, the three-dimensional carbon nanostructured porous foam 102 may be exposed to solar radiation or a concentrated solar power energy source 104.

In one embodiment, the three-dimensional carbon nanostructured porous foam 102 may be mixed into sands or soils. The three-dimensional carbon nanostructure porous foam material "heat exchangers" can be mixed into stagnant or flowing solids such as sands or soils mixed and contaminated with any of the said fluids to be liberated.

In one embodiment, the three-dimensional carbon nanostructured porous foam 102 may be contained in a continuous loop such as a pipe or tube or hose, allowing a continuous flow of the substance element 106 through the three-dimensional carbon nanostructured porous foam 102. The three-dimensional carbon nanostructured porous foam 102 may simultaneously act like a filter membrane. The substance may be continuously filtered through the three-dimensional carbon nanostructured porous foam 102 via pressurized liquid/gas fed through the open pores of the three-dimensional carbon nanostructured porous foam 102. In one variation, it may also be possible to perform separation of individual components that make up a multiphase or heterogeneous mixture by pore size of the three-dimensional carbon nanostructured porous foam 102.

The three-dimensional carbon nanostructured porous foam 102 can be made in various ways all of which are within the scope and spirit of the present teachings, any specifically listed renderings should only be considered as examples for illustrative purposes. One possible carbon foam candidate the three-dimensional carbon nanostructured foam synthesized via chemical vapor deposition (CVD) as found in reference U.S. patent application Ser. No. 13/424,185 to Daniel Paul Hashim et. al., entitled "Methods of synthesizing Three-Dimensional Heteroatom-Doped Carbon Nanotube Macro Materials and Compositions Thereof," filed on Mar. 19, 2012 and published under U.S. Patent Application Publication No. US 2012/0238021 A1 on Sep. 20, 2012.

The three-dimensional carbon nanostructured porous foam 102 may also be synthesized via fluidized bed catalytic chemical vapor deposition (FB-CCVD), freeze-drying process of the individual carbon nano-scaled elements, pyrolysis of polymers or other organic materials, and/or electrospinning process technique. The three-dimensional carbon nanostructured porous foam 102 may be composed of carbon nanostructures obtained from exfoliation methods.

The substance element 106 may be a liquid or gas substance and the substance element 106 may or may not contain particulate solids. The substance element 106 fluid may be crude oil, tar, soot, water, steam, carbon dioxide, alcohols, natural gas, organics, alkanes or paraffins, cycloalkanes or naphthenes, asphaltene and other bituminous products, hydrogen, hydrogen sulfide, aromatic hydrocarbon compounds and other hazardous chemicals, or any other petrochemical processed fluids and/or gases or any combination thereof. Substance element 106 may be composed of a mixture of many different molecules. In one variation, it may also be possible to perform separation of individual components that make up a multiphase or heterogeneous mixture by varying the electronic energy source 104 energy in order to allow different temperature zones and distillation of the desired substance element 106.

In one embodiment, the electronic energy source 104 may produce microwave radiation at the conventional microwave oven frequency of 2.45 GHz. Other potential frequency ranges vary between 300 MHz and 300 GHz, however literally any frequency range may be employed to radiate the absorbed, flowing or stagnant substance element 106 so as to improve upon the absorption efficiency and penetration depth of the radiation into the three-dimensional carbon nanostructured porous foam 102. The electronic energy source 104 power may be adjusted accordingly so as to prevent overheating or to adjust the heating rate. The electronic energy source 104 may be pulsed or continuous. The electronic energy source 104 may be directed using a waveguide so as to heat specific portions of the three-dimensional carbon nanostructured porous foam 102. The electronic energy source 104 may be a gun source and have waveguides to direct the electronic energy source 104 radiation to designated parts of the three-dimensional carbon nanostructured porous foam 102 as necessary.

Figure 2:
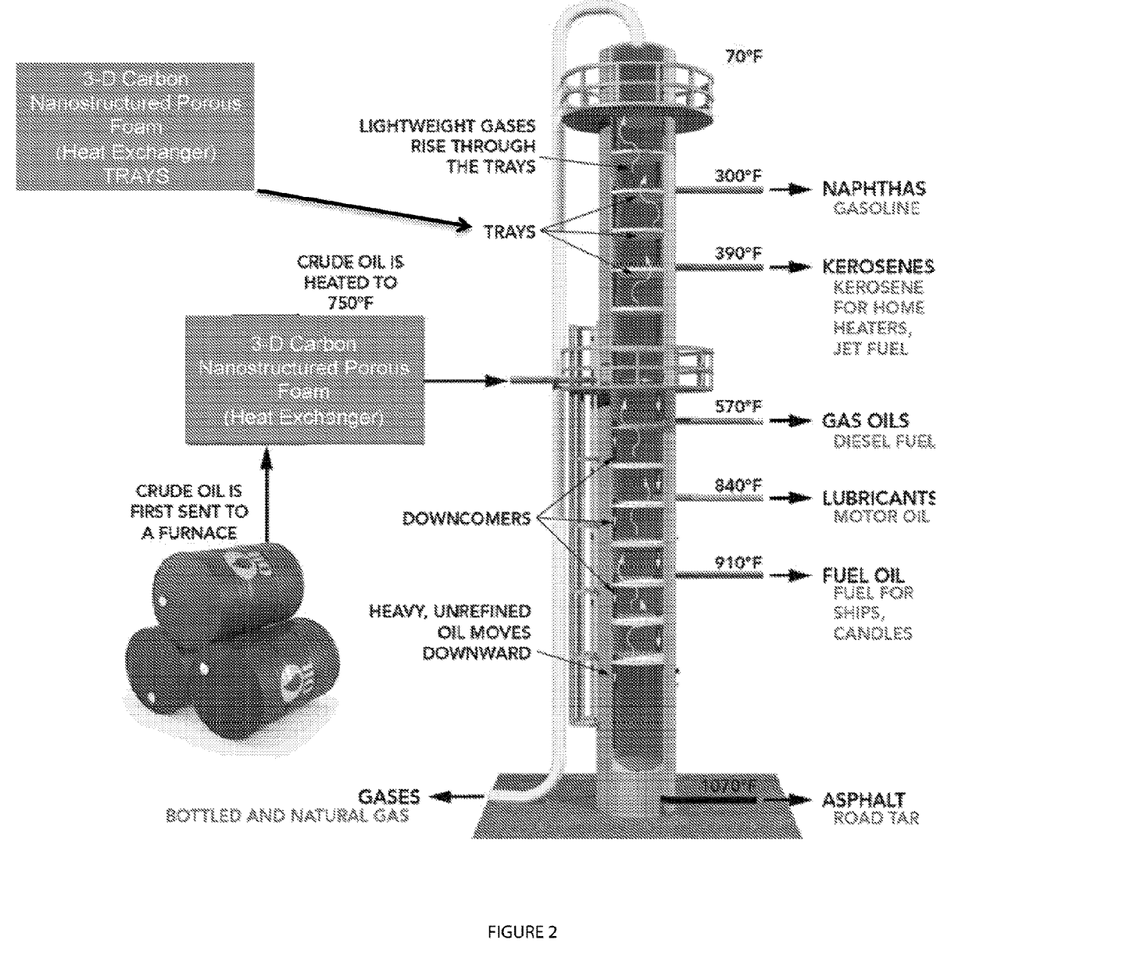
FIG. 2: Exemplifies where the three-dimensional carbon nanostructured porous foam may be used as a heat exchanger unit designed specifically for refining crude oil and installed in an Oil & Gas refinery distillation column.

In one embodiment, the three-dimensional carbon nanostructured porous foam 102 may be used as a heat exchanger unit designed specifically for refining crude oil and installed in an Oil & Gas refinery as depicted in FIG. 2. With pulses of microwave energy from electronic energy source 104 at different pulse rates, the three-dimensional carbon nanostructured porous foam 102 temperature can be set at any specific temperature through PDI controller like feedback system. In this way, each component contained in the crude oil can be distilled or fractionated out of the three-dimensional carbon nanostructured porous foam 102 with high uniformity and high output efficiency.

Embodiments of the present teachings can be used as a macro-scaled or micron-scaled heat exchanger element to be injected downhole via any enhanced oil recovery (EOR) technique and subsequently the downhole environment can be injected with microwave radiation so as to heat up the three-dimensional carbon nanostructured porous foam "heat exchanger" element 102 in order to heat up and vaporize out the oil resource out of the surrounding downhole environment.

As a part of the electromagnetic spectrum, microwaves heat materials fast and efficiently via direct energy transfer, while conventional heating methods rely on conduction and convection. To date, the use of microwave heating in the research of carbon-based materials has been mainly limited to liquid solutions. However, more rapid and efficient heating is possible in electron-rich solid materials, because the target materials absorb the energy of microwaves effectively and exclusively. Carbon-based solid materials are suitable for micro-wave-heating due to the delocalized pi electrons from sp2-hybridized carbon networks.

Microwaves are a part of the electromagnetic spectrum with frequencies ranging from 300 MHz to 300 GHz, lying between infrared and radio frequencies. Microwave technologies were developed rapidly during and after the Second World War for radar and communication uses. These days, microwaves are extensively used for wireless communications, such as long term evolution; for major wireless local area network standard (Wi-Fi); space craft communication and radar applications like global positioning system; and air traffic control. In addition to the radar and communication uses, microwaves are also widely used for heating. Foods are rapidly and conveniently heated by a microwave oven at home, and a variety of materials are heated at industries and laboratories using microwaves.

Microwave heating provides several advantages over conventional (ring or resistive) heating, most of which come from the way energy is delivered. Microwaves can deliver their energy directly to target materials by radiation at the speed of light without conduction or convection, the main processes of energy transfer in conventional heating. Thus, microwave heating is much faster than conventional heating, and selective heating is possible without interaction between the microwaves and their surroundings.

Research on the microwave heating of carbon-based materials can be classified into two categories depending on the phase of microwave absorber. One is solution heating, rep-resented by microwave-assisted organic synthesis (MAOS) and the other is solid heating, whose main targets are solid state carbons and metals. Solution and solid heating differ greatly, both in the heating mechanism and the accompanying reactions.

The difference in the heating mechanism for a solution and a carbon-based solid is important to understand. Microwave heating of a solution is mainly related to the dipole rotation of polar solvent molecules. However, in electron-rich solids which have no freely-rotatable dipoles, like carbon-based solids, it is the motion of electrons that generates heat, through joule heating within the grain, or arc generation at phase boundaries.

Polarizations under microwaves: When a dielectric material, whose charged particles can't move freely, is exposed to an external electric field, the electric charges cause dielectric polarization, which arises from the dis-placement of charges from their average equilibrium position. This polarization can be categorized as follows: 1) electronic polarization by displacement of electrons from the nuclei, 2) atomic polarization by displacement of atomic nuclei, 3) dipolar polarization by reorientation of molecules which have permanent dipoles, and 4) interfacial polarization by accumulation of relatively mobile charges at grain/phase boundaries or surfaces.

Microwaves are a kind of electromagnetic wave, and consequently, the direction and the magnitude of their electric field changes continuously with time, so the polarization they induce is also changed with time. In general, polarization has a phase lag with the electric field oscillation because a material's polarization does not respond instantaneously to an applied field. Therefore, permittivity (e), which describes the electric field flux generated by polarization, is usually expressed as a complex form (e'+ie") to show the magnitude and the phase of polarization at the same time. Here, the real part of permittivity (e') is related to the stored energy within the medium and the imaginary part of the permittivity (e") is related to the energy dissipated as heat.

When the frequency of an electric field oscillation is increased over a certain point, some polarization stops contributing to the total polarization because there is an increasing phase lag between the electric field oscillation and reorientation of the polarization. In this case, the real part of the permittivity decreases while the imaginary part of the permittivity decreases, which means the dissipation of energy in the form of heat increases.

Electronic polarization and atomic polarization don't contribute to microwave absorption because they start to have phase lag at a frequency higher than the microwave frequency. Generally, interfacial polarization occurs far below the micro-wave frequency, but the peak frequency of dielectric loss factor of interfacial polarization can vary considerably according to the conductivity and dielectric properties of the material. Thus, interfacial polarization as well as dipolar polarization are considered to be the polarizations involved in microwave heating.

Microwave heating of a solution is explained by dipolar polarization and ionic conduction. Most solvents including water, dimethylformamide, tetrahydrofuran and ethanol have permanent dipoles. When a microwave is applied, the dipoles rotate with a delay to the change of the electric field, which causes friction and heat. In addition, the solution is also heated by ionic conduction when ions exist.

As a result, most reactions can be carried out using polar solvents even when the microwave absorbance of the reactant is poor. On the other hand, the method has some limitations, as follows: 1) most of the microwave energy used for the heating of polar solvents is dissipated, and 2) there is no macroscopic difference in the distribution of temperature within the reactor, while the absorption of microwave energy may be selective.

In the case of carbon-based solids which have few or no freely rotating dipoles, microwave heating can't be explained as above. Instead, the interaction between microwaves and electrons is important. Microwave heating of carbon-based solids is mainly explained by interfacial polarization (so called Maxwell-Wagner-Sillars [MWS] polarization). In addition, carbon-based solids possess semiconducting features because of delocalized pi-electrons in the graphitic region, so Joule heating also plays an important role in the heating of carbon-based solids by microwave.

In these cases, unlike solution heating, microwave heating is very efficient and selective because the microwave energy is solely absorbed by the target material.

CNTs have excellent electrical properties resulting from sp2-networks of carbon atoms. The number of free electrons which can migrate freely over the whole of the layer is about one per each carbon atom. The free electrons enable CNTs to absorb microwave energy considerably and to be heated effectively by microwaves.

Figure 3:
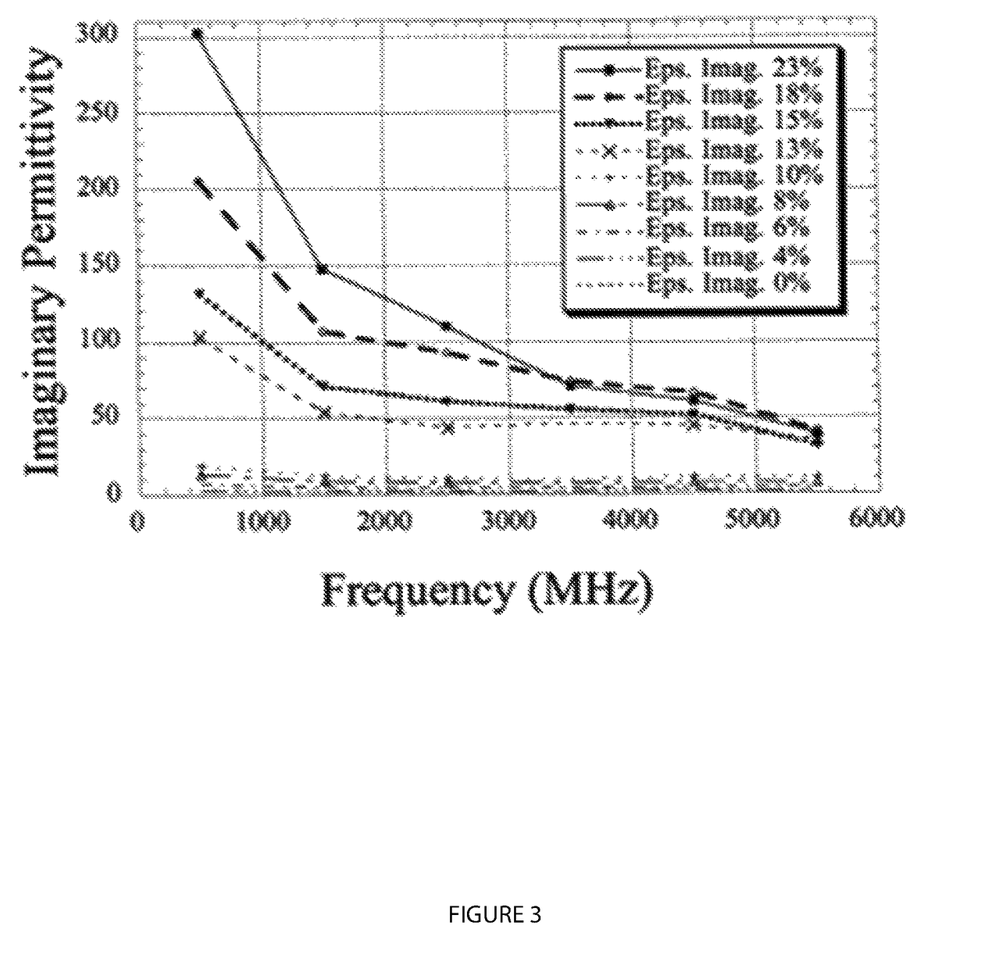
FIG. 3: Imaginary (e") part of permittivity spectra of polymer composites with 0-23 wt % of single-wall carbon nanotubes.

The microwave absorbing property of CNTs was measured by Grimes et al. [Grimes C A, Mungle C, Kouzoudis D, Fang S, Eklund P. C. The 500 MHz to 5.50 GHz complex permittivity spectra of single-wall carbon nanotube-loaded polymer composites. Chem Phys Lett, 319, 460 (2000). http://dx.doi.org/10.1016/S0009-2614(00)00196-2] for the first time in 2000. Complex permittivity of 0-23 weight percent single-wall CNTs (SWCNTs) dispersed in poly-ethylmethacrylate composites was measured in the frequency range from 500 MHz to 5.5 GHz as shown in FIG. 3. With 23 weight percent of SWCNTs, the imaginary part of the complex permittivity was increased by a factor of 1200 at 500 MHz and measured over 100 at 2.45 GHz.

In 2003 Imholt et al. [6] reported various observations of microwave-CNTs reaction with temperature measurement. Microwave irradiation (2.45 GHz, 700 W) on HiPco-generated SWCNTs showed strong microwave absorption with light emission, heat release, outgassing and nanotube reconstruction. The temperature reached 2000° C. during the reaction and $H_2$ expulsion was observed by a residual gas analyzer. CNTs after microwave irradiation showed welded and looped nanotubes which were not present in the original HiPco SWCNTs.

Among the various applications of microwave heating of CNTs, CNT/polymer welding is the most actively researched area. Unlike other CNT/polymer composite making techniques such as solution mixing, melt mixing and in-situ polymerization [16], microwave welding gives several advantages.

The first advantage is that microwave welding can be done within a few minutes. Specifically, Wang et al. [8] reported CNTs subsided into a poly(ethylene terephthalate) (PET) substrate after only 1 s of microwave irradiation. A second advantage is the selectiveness of the heating. Because the microwave absorbance of most polymers is negligible, only CNTs absorb the microwave energy and are heated. So, welding can be performed without significantly affecting the bulk polymer.

In general, the use of microwave radiation as an electronic energy source 104 to generate heat is not harnessed by many materials aside from water exploited by conventional domestic microwave units or industrial microwave units, and is certainly not exploited in the state of the art heat exchangers used in many other industrial applications including petrochemical processing units, refineries, power plants, and enhanced oil recovery to name a few. The concept of a microwave volumetric heating (MVH) unit is especially not exploited in the Oil & Gas industry in particular. Part of the reason for this is, not many materials are capable of absorbing microwave radiation so efficiently outside of water. It is important to note that only fluid substances containing polar molecules like water can absorb microwaves and fluid substances such as organics and oils of non-polar molecules cannot absorb microwaves efficiently.

It is also known that carbon also absorbs microwaves quite efficiently. The use of nanotechnology in state of the art heat exchanger applications in the form of nanoscale carbon merely entails dispersions of the individual nanoscale elements in the form of powder into a solid matrix material. However, the use of individual nanoscaled elements of carbon dispersed in a free-form manner is not an ideal situation for microwave volumetric heating of continuously flowing fluids and gases for the following reasons: (1) is very difficult to achieve uniform dispersions of carbon nanostructures, (2) they will not allow for uniformly heating as they are not fixed in three dimensional space, (3) loosely dispersed free-form powders of individual nanoscale elements and their nanostructure bundled form will be lost or easily carried away in the fluid/gas streams, (4) loosely dispersed free-form powders of individual nanoscale elements and their nanostructure bundled form will backwash and contaminate the fluid/gas streams and (5) dispersed individual elements cannot be easily salvaged and handled in a practical and feasible manner. For these reasons, a three-dimensional carbon nanostructured porous foam In one embodiment, the three-dimensional carbon nanostructured porous foam 102 may be used as a heat exchanger unit designed specifically for refining crude oil detailed in the present teachings is valuable as a commercially viable method for the use of carbon nanostructures in Microwave Volumetric Heating (MVH) of heating liquids, suspensions, gases or solids in a continuous flow on an industrial scale.

The materials which interact with microwaves to produce heat are called microwave absorbers. The ability of a material to be heated in the presence of a microwave field is defined by its dielectric loss tangent: $\tan \delta = \varepsilon''/\varepsilon'$. The dielectric loss tangent is composed of two parameters, the dielectric constant (or real permittivity), $\varepsilon'$, and the dielectric loss factor (or imaginary permittivity), $\varepsilon''$; i.e., $\varepsilon = \varepsilon' - i\varepsilon''$, where e is the complex permittivity. The dielectric constant ($\varepsilon'$) determines how much of the incident energy is reflected and how much is absorbed, while the dielectric loss factor ($\varepsilon''$) measures the dissipation of electric energy in form of heat within the material. For optimum microwave energy coupling, a moderate value of $\varepsilon'$ should be combined with high values of $\varepsilon''$ (and so high values of $\tan \delta$), to convert microwave energy into thermal energy. Thus, while some materials do not possess a sufficiently high loss factor to allow dielectric heating (transparent to microwaves), other materials, e.g. some inorganic oxides and most carbon materials, are excellent microwave absorbers. On the other hand, electrical conductor materials reflect microwaves. For example, graphite and highly graphitized carbons may reflect a considerable fraction of microwave radiation. In the case of carbons, where delocalized π-electrons are free to move in relatively broad regions, an additional and very interesting phenomenon may take place. The kinetic energy of some electrons may increase enabling them to jump out of the material, resulting in the ionization of the surrounding atmosphere. At a macroscopic level, this phenomenon is perceived as sparks or electric arcs formation. But, at a microscopic level, these hot spots are actually plasmas. Most of the time these plasmas can be regarded as microplasmas both from the point of view of space and time, since they are confined to a tiny region of the space and last for just a fraction of a second. An intensive generation of such microplasmas may have important implications for the processes involved.

Figure 4:
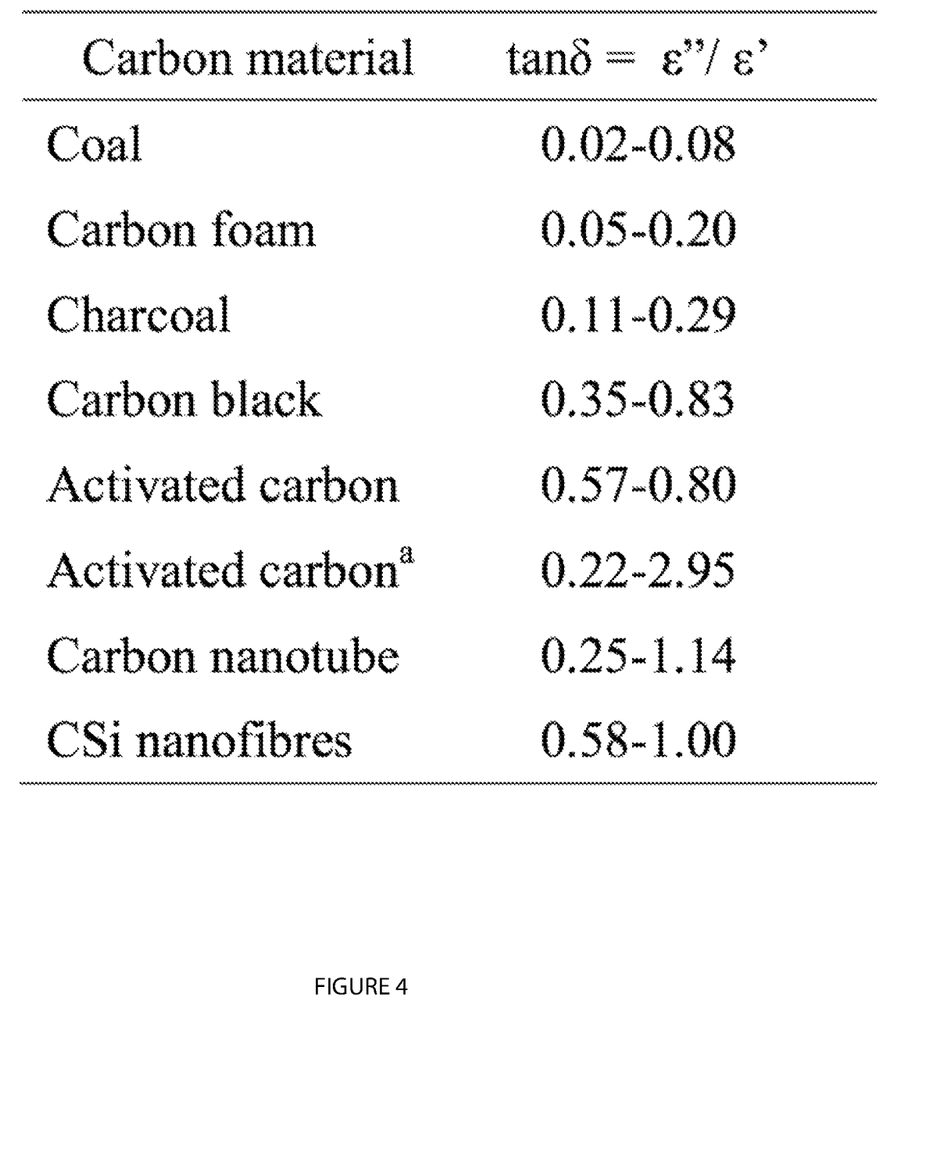
FIG. 4: Dielectric loss tangents for different carbon materials at a frequency of 2.45 GHz and room temperature, ca., 298 K.

The microwave heating of a dielectric material, which occurs through the conversion of electromagnetic energy into heat within the irradiated material, offers a number of advantages over conventional heating such as: (i) non-contact heating; (ii) energy transfer instead of heat transfer; (iii) rapid heating; (iv) selective material heating; (v) volumetric heating; (vi) quick start-up and stopping; (vii) heating from the interior of the material body; and, (viii) higher level of safety and automation. Due to these advantages, microwaves are used in various technological and scientific fields in order to heat different kinds of materials. Most of the industrial applications of microwave heating are based on heating substances that contain polar molecules, for example: food processing, sterilization and pasteurization, different drying processes, rubber vulcanization, polymerization or curing of resins and polymers by elimination of polar solvents, etc. In addition, solid materials with a high dielectric loss factor, i.e., microwave absorbers, can be subjected to different processes based on microwave heating. Among these materials, carbons are, in general, very good microwave absorbers, so they can be easily produced or transformed by microwave heating. Moreover, carbon materials can be used as microwave receptors to indirectly heat materials which are transparent to microwaves. Thus, carbon materials have been used as microwave receptors in soil remediation processes, the pyrolysis of biomass and organic wastes, catalytic heterogeneous reactions, etc. The high capacity of carbon materials to absorb microwave energy and convert it into heat is illustrated in FIG. 4, where the dielectric loss tangents of different carbons are listed. As can be seen, the loss tangents of most of the carbons, except for coal, are higher than the loss tangent of distilled water (tan δ of distilled water=0.118 at 2.45 GHz and 298 K). The search and compilation of these data is no a straightforward matter. Although this parameter is helpful for the study of microwave heating, few research groups have determined the dielectric loss tangents of carbons.

The nanoscale of the three-dimensional carbon nanostructured porous foam 102 heat exchanger is responsible for the superior performance when compared to the current state of the art heat exchangers commonly used in commercial and industrial applications. The properties of the three-dimensional carbon nanostructured porous foam 102 have increased surface area and incredibly high porosity and low density allowing for more substance to be in direct contact with the heat source allowing for more efficient heat transfer. More notably, the three-dimensional carbon nanostructured porous foam 102 is superior to the state of the art of any carbon nanotechnology-based microwave heat exchanger inventions because it allows for microwaves to transfer heat to a continuous flow of gases and fluids via microwave radiation and not merely solids or stagnate fluids that have been dispersed with nanoscale carbon nanomaterial elements. Another issue to note is the non-uniformity and lack of stability of dispersed carbon nanomaterials where embodiments of the present teachings do not have those issues due to being a porous three-dimensional solid framework of individual nanoscale elements that holds its mechanical structure uniformly within the fluid, gas, or solid even throughout the heating and evaporation cycle process. It is absolutely necessary to have a porous material like this three-dimensional carbon nanostructured porous foam 102 to allow for a flowing gas or liquid to pass through the carbon nanostructure heating elements in order to efficiently and uniformly transfer heat. Along these lines, the three-dimensional carbon nanostructured porous foam 102 is superior because it solves the problems outlined above by exploiting the nanoscaled carbon materials in a unique three-dimensional carbon nanostructured porous foam 102 as a micro- or even macro-scaled foam solid material. In the present teachings, the active heat exchanger materials are carbon nanoscaled elements presented in a more feasible form—a safe-to-handle three-dimensional carbon nanostructured porous foam 102 form, rendering it more suitable for large-scale industrial applications of MVH.

The three-dimensional carbon nanostructured porous foam 102 may be used in the refining industry. In petrochemical refineries and the oil and gas industry to make crude oil. In the first step of commercial crude oil refining, the crude oil is heated from 21° C. to 343° C. prior to entering the distillation column. A series of conventional shell and tube heat exchangers typically exchange heat between crude oil and other oil streams to heat the crude to 260° C. prior to heating in a furnace. The three-dimensional carbon nanostructured porous foam 102 may be used here to replace the conventional heat exchanger units. Within the distillation column (fractionation tower) the novel heat exchanger of the present method can be used in the series of horizontal condensation trays that divide the column at intervals and are each held at a constant temperature set just below the boiling point of the desired hydrocarbon to be collected at that tray. Thermal "cracking" processing units can utilize the novel heat exchanger of the present teachings to convert the large (heavy) molecular hydrocarbons and make the smaller, lighter molecules such as gasoline and jet fuel. The three-dimensional carbon nanostructured porous foam 102 may also be used in oil shale refining, to efficiently remove unusable oil from shale via novel heat exchanger materials, and natural gas processing.

Additional applications include: water desalinization (i.e. membrane-thermal hybrid desalinization heat exchanger materials); power plants and steam power generation (i.e. utilize the membrane-thermal hybrid approach to generate steam more efficiently via microwave radiation assistance); enhanced oil recovery (i.e. addition of carbon nanostructured foam heat exchanger materials to the water flooding injection method downhole where later microwaves); heat generation source for aerospace industry; thermal decomposition of waste disposal; catalysis; space heating; refrigeration; commercial heating ventilation and air conditioning (HVAC) system; power stations; chemical plants; petrochemical plants; and sewage treatment.

In one embodiment the three-dimensional carbon nanostructured porous foam 102 may function as a microwave regeneration filter (e.g. fuel filters, diesel particulate filters, etc.). It can be used as an advanced thermal-membrane hybrid and also for its ability to be easily regenerated. When soot is built up in the filter from the fuel or carbonaceous exhaust through the filter, the filter gets clogged and creates a larger pressure drop across the filter and thereby decreases the performance. This requires the filter to be regenerated to renew the filter performance. Utilizing the present method and system provides the following advantages: reduced electric load on vehicle's alternator/battery system; reduced engine back pressure due to more frequent regeneration; faster regeneration without damage to filter media; reduced size and weight of the filter system; and reduced costs of the ceramic filter medium.

Another topic of investigation has been the microwave-induced regeneration of exhausted activated carbons. Thus, Price et al. [58] and Cha et al. [59] have reported microwave-assisted regeneration processes of activated carbon saturated with volatile organic compounds (VOC). As well as of carbons used in gas phase applications, the regeneration of activated carbons used in liquid phase adsorption has been studied. Thus, different activated carbons polluted with phenol [60] and pharmaceuticals [61] have been subjected to thermal regeneration under $N_2$ and $CO_2$ atmospheres, using both conventional and microwave heating. It was found that the rapid heating of the exhausted activated carbons by microwave energy leads to a quick regeneration. Furthermore, microwave technology allowed the activated carbons to be recycled and reused several times. Thus, it was shown that microwave heating preserves the porous structure of the regenerated activated carbons more efficiently than treatment in a conventional device. The use of this technique causes no damage to the carbon; rather, it increased the surface area, at least during the first regeneration cycles [62]. FIG. 3 illustrates the changes in the adsorptive capacity of a commercial activated carbon exhausted with phenol, after subsequent cycles of regeneration at 1123 K in $N_2$ and $CO_2$ atmospheres, using both conventional and microwave heating. Interestingly, regeneration in the microwave oven doesn't just preserves (or even increases) the adsorptive capacity of the activated carbon, the regeneration time is reduced by 90% as well.

Microwave heating has been investigated for use in various metallurgical processes, including pyrometallurgy, hydrometallurgy [63] and mineral processing [3].

Yet in the particular case of processes involving carbons, the microwave-assisted reduction of metal oxides with different carbon materials has been extensively investigated. Thus, hematite fines and magnetite concentrates have been mixed with different carbons like charcoal or coke and then subjected to microwave heating up to 1273 K [64]. It was found that the process is influenced by the type of carbon used and that, under similar conditions of temperature, microwave reduction produces better results than those attained by conventional heating. Recently, a process for carrying out the carbothermic reduction of iron oxides using microwave heating has been patented [65]. Similar processes that combine microwave heating with the use of various kinds of carbons as reducing agent and microwave absorbers are applied to other metallic oxides [66].

Microwave heating is also employed in the gold mining industry to recover gold from the activated carbon used in the so called carbon-in-pulp process (CIP). The carbon, which is used to adsorb the gold cyanide molecule, is periodically removed from the adsorption tanks to allow removal of the gold by elution. Then, after the carbon is subjected to an acid wash to remove inorganic compounds, it is regenerated at 923-1123 K in a steam atmosphere to remove other foulants such as flotation reagents, lubricating oils and humic acids which would foul the carbon and undermine its performance. The regenerated carbon is then sized and returned to the CIP circuit.

Regeneration is conventionally done in rotary kilns or vertical tube furnaces. However, it has been demonstrated that the use of microwave heating can be also an alternative economically feasible, with a saving of energy and time consuming [67].

Another field of application of microwave heating is the processing of coals. Coals are, in general, very poor microwave absorbers (see FIG. 4), since they do not possess graphene lattices of a size large enough to allow delocalized π-electrons to move in order to couple with the electromagnetic field of the microwaves (i.e., heating by interfacial polarization). Thus, only devolatized coals, chars or cokes, with a relatively large amount of delocalized π-electrons that move on the incipient graphenic structures, show good microwave absorbance properties.

Despite this, the microwave heating of coals is used in the industrial processing of coal. For example, a process for the microwave-assisted grinding of coals has been described [68]. In this process, coals of various ranks were exposed to microwave radiation to quantify the effect on grindability. Reductions of up to 50% of relative grindability were reported after 5 minutes of microwave exposure. These reductions are believed to be due to fracture mechanisms; inherent moisture within the coal structure absorbs microwaves changing phase, and producing considerable pressure and differential expansion by gangue mineral components. Another example is the microwave-assisted desulphurization of coals which is based on the fact that pyrite heats more rapidly than coal. This heating has the effect of enhancing the magnetic susceptibility of pyrite thereby improving the removal rates by magnetic separation [69]. In addition to these two industrial applications of microwave heating of coals, the possibility of using microwave heating of a high volatile bituminous coal for rapid coke making has been studied at the bench scale [70]. It is suggested that devolatilization starts due to the moisture content and —OH bonds present in the coal, and then, when the aromaticity of the devolatilized material increases, the absorption of microwaves allows temperatures in excess of 1273 K, which produces graphitized coke in less than 2 h.

Microwave heating is a good alternative for carrying out the pyrolysis of biomass [71, 72], coal [73, 74], oil shale [75, 76], glycerol [77] and various organic wastes [78]. In general, these materials are poor receptors of microwave energy, so they cannot be directly heated up to the high temperatures usually required to achieve total pyrolysis. However, microwave-induced pyrolysis is possible if the raw material is mixed with an effective microwave receptor, such as certain metal oxides [73, 74] or carbon materials [50, 71, 72, 75-78]. The latter are usually preferred for this particular application, not only because they are very good microwave absorbers, but also because they are inexpensive, easily available in different textures, sizes, forms, etc; and do not add any extra inorganic component to the solid residues obtained after pyrolysis. Moreover, the carbonaceous residue itself which is obtained from the pyrolysis of the organic materials can be used as an excellent microwave absorber.

A case of particular interest is the pyrolysis of sewage sludge [50, 79-85], often called biosolids. Handling of this waste, which can be considered as biomass, represents a challenge in industrialized countries. So far, none of the methods used, from land reclamation, such as landfill or organic fertilizers, to incineration, is exempt from drawbacks, like collateral pollution or high costs of treatment. These high costs are in part due to the need to remove the high water content of the sludge. Microwave heating could be a highly efficient alternative for drying these biosolids [81]. Moreover, a process that uses the steam produced by microwave drying to gasify the products generated during subsequent pyrolysis has been described [80]. In this method, drying, pyrolysis and gasification of the sewage sludge take place at the same time, giving rise to a larger gas fraction with a high syngas ($CO+H_2$) content [79, 84, 85] and to an oil fraction with a low polycyclic aromatic hydrocarbons (PAHs) content [82, 83]. In contrast, the oil from the conventionally heated sludge consists primarily of PAHs. Unlike other conventional pyrolysis methods and due to the high temperatures that are reached during the process, a partially vitrified solid residue can be obtained by microwave-assisted pyrolysis [80]. This is particularly useful in the case of sludges with high heavy metal content.

Biofuels Production: A unique characteristic of microwave-assisted thermal treatments of biomass and biosolids is that they produce a considerable higher amount of $H_2$ and CO (syngas) and much less $CO_2$ than similar treatments carried out using conventional heating. Given that microwave-assisted pyrolysis maximizes the gas fraction obtained (oils are produced but in very small amounts) and the fraction of the carbonaceous residue can be used as microwave receptor and consumed by auto-gasification with the $CO_2$ obtained in the process [72], this method can be used for the thermal valorization of biomass and biosolids, by producing mainly syngas-rich gases.

Microwave heating combined with the use of carbons as microwave receptors has also been used in soil remediation to eliminate organic pollutants. Thus, the use of graphite fibres, as microwave receptor, in microwave-assisted extraction (MAE) has been shown to be a successful method for the extraction of contaminants in soils, rivers and marine sediments [86]. Similar microwave-induced thermal treatments employing granular activated carbon as microwave absorber to achieve the appropriate temperature were used to decontaminate the soil.

Owing to their particularly strong interaction with microwave radiation and high thermal conductivity, graphite and certain other carbons are efficient sensitizers. They are capable of converting radiation energy to thermal energy, which is then transmitted instantaneously to supported chemical compounds. Two types of reaction are favored by carbons-microwave coupling: (i) reactions which require a high temperature, and (ii) reactions involving chemical compounds which, like the organic compounds, have a low dielectric loss and do not heat up sufficiently under microwave irradiation. Thus, microwave heating is a valuable, non-conventional energy source for organic synthesis, which can produce spectacular accelerations in many reactions [88]. Carbons and carbon-supported catalysts are used as sensitizer or sensitizer-plus-catalyst in several organic microwave-assisted synthesis reactions, such as Diels-Alder reactions, the thermolysis of esters, the decomplexation of metal complexes, the pyrolysis of urea, sterifications, etc. [89]. Carbon particles are used to selectively heat the catalyst and substrate without bulk heating the solution. A case of particular interest is fullerene chemistry under microwave irradiation [90], where fullerenes are subjected to different organic reactions in order to functionalize them.

Carbons can be used as catalyst in a variety of heterogeneous gas-phase catalytic systems [91]. Besides, they are good microwave absorbers. These two characteristics have been combined to enhance various catalytic reactions, in which carbons play the double role of catalyst and microwave receptor. In fact, the interaction of microwave irradiation with some heterogeneous catalytic systems has been proven to enhance the reaction rates, the selectivities of the products and the conversion values.

Figure 5:
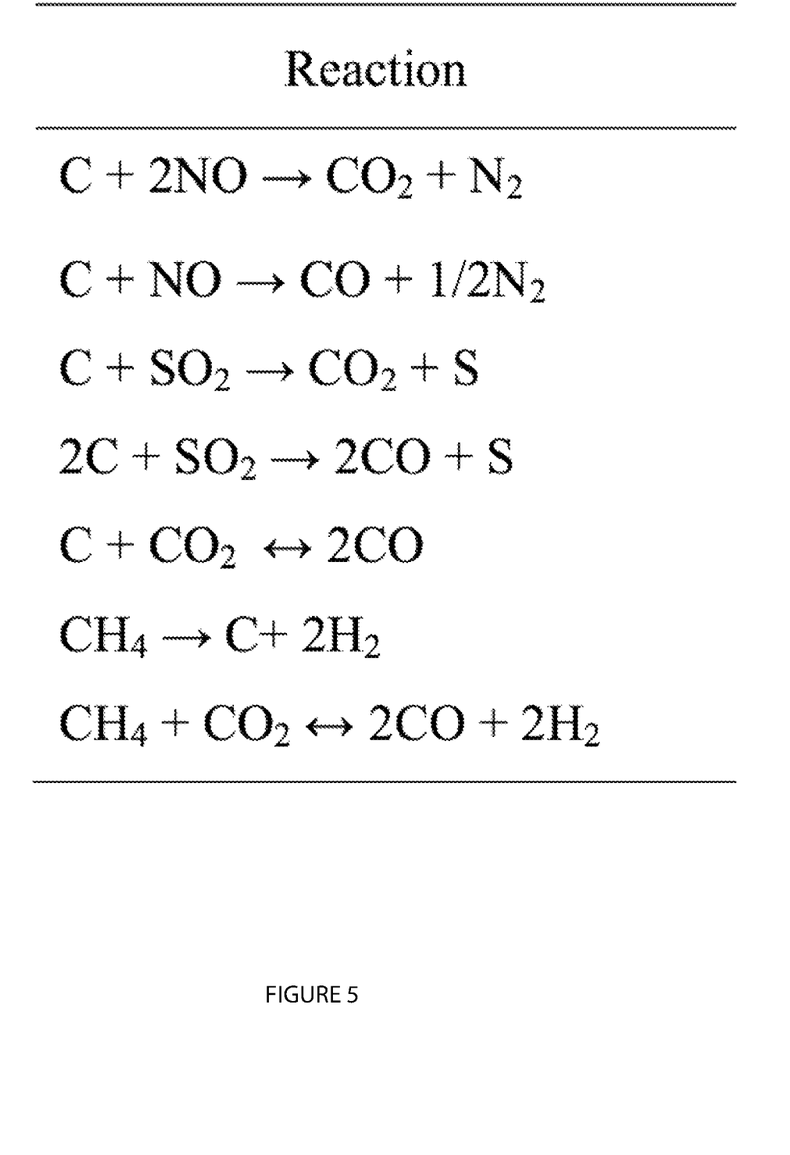
FIG. 5: Examples of microwave-enhanced heterogeneous catalytic reactions, in which carbons are used as catalysts and microwave receptors.

$NO_X$ reduction [95, 96], $SO_2$ reduction [97], catalytic $CH_4$ decomposition for $H_2$ production [98, 99] and $CO_2$ reforming of $CH_4$ (dry reforming) [100, 101] are just some examples in which the use of carbon materials as catalyst and microwave receptor resulted in a considerable improvement in the yield of the reactions. A variety of carbon materials, such as activated carbons, metallurgical cokes, chars or anthracite, were used. Several microwave-enhanced heterogeneous catalytic reactions, in which carbons acted as catalyst and microwave receptor, are shown in FIG. 5.

The improvement in the results is attributed to the way the catalyst is heated by microwaves. Thus, in the case of microwave heating, the catalyst (i.e., the carbonaceous material) is heated directly by the action of the microwaves, and so it is at a higher temperature than the surrounding atmosphere. However, under conventional heating, heat is transferred through the surface of the catalyst, mainly by conduction and convection, resulting in a totally different temperature gradient. In addition to this, as mentioned before, microplasmas are commonly produced during the microwave irradiation of carbons. The temperature in these microplasmas (also called hot spots) is believed to be much higher than the overall temperature of the system, which usually favors heterogeneous reactions between the solid catalyst and the gases taking part in the reaction. It should therefore be possible to apply this technique to other catalytic reactions in which a carbon-based catalyst is used.

The temperature range of heating of the carbon can be from room temperature to well over 2000° C. depending on the level of oxygen in the environment before oxidation occurs.

The three-dimensional carbon nanostructured porous foam 102 may be decorated with nanoparticles of a metal, metal oxide, semiconductor, or any combination thereof adsorbed on the surface of the nanostructures for enhanced catalytic behavior of a desired reaction of the flowing or stagnant fluid to alter the 106 chemical/physical state to the 108 chemical/physical state.

The three-dimensional carbon nanostructure porous foam material may be composed of carbon nanotubes or heteroatom doped carbon nanotubes or graphene, heteroatom doped graphene, graphitic microfibers, or graphene oxide or any combination thereof.

Alternative implementations are suggested, but it is impractical to list all alternative implementations of the present teachings. Therefore, the scope of the presented disclosure should be determined only by reference to the appended claims, and should not be limited by features illustrated in the foregoing description except insofar as such limitation is recited in an appended claim.

While the above description has pointed out novel features of the present disclosure as applied to various embodiments, the skilled person will understand that various omissions, substitutions, permutations, and changes in the form and details of the present teachings illustrated may be made without departing from the scope of the present teachings.

Each practical and novel combination of the elements and alternatives described hereinabove, and each practical combination of equivalents to such elements, is contemplated as an embodiment of the present teachings. Because many more element combinations are contemplated as embodiments of the present teachings than can reasonably be explicitly enumerated herein, the scope of the present teachings is properly defined by the appended claims rather than by the foregoing description. All variations coming within the meaning and range of equivalency of the various claim elements are embraced within the scope of the corresponding claim. Each claim set forth below is intended to encompass any apparatus or method that differs only insubstantially from the literal language of such claim, as long as such apparatus or method is not, in fact, an embodiment of the prior art. To this end, each described element in each claim should be construed as broadly as possible, and moreover should be understood to encompass any equivalent to such element insofar as possible without also encompassing the prior art. Furthermore, to the extent that the term "includes" is used in either the detailed description or the claims, such term is intended to be inclusive in a manner similar to the term "comprising".

What is claimed is:

1. A system for heating, evaporating, vaporizing, distilling, decomposing, pyrolyzing, cracking or refining a stagnate or flowing substance, comprising:
    a) a solid three-dimensional carbon nanotube structures comprising heteroatom-doped carbon nanotubes, having a plurality of porous cavities, and
    b) an energy source, adapted to transfer electromagnetic radiation to the carbon nanostructure porous foam material at a predetermined frequency bandwidth,
    wherein the energy source comprises radio/microwave radiation.

2. The system of claim 1, wherein the porous cavities of the solid three-dimensional carbon nanotube structures comprising heteroatom-doped carbon nanotubes are decorated with metals, metal oxides, or semiconductors.

3. The system of claim 2, wherein the solid three-dimensional carbon nanostructured porous foam material nanotube structures comprising heteroatom-doped carbon nanotubes is macro-scaled.

4. The system of claim 1, wherein the heteroatom is boron.

5. The system of claim 1, wherein the pores of the solid three-dimensional carbon nanostructured porous foam material are in contact with a stagnate.

6. The system of claim 1, wherein the pores of the solid three-dimensional carbon nanostructured porous foam material are in contact with a flowing substance.

7. A system for heating, evaporating, vaporizing, distilling, decomposing, pyrolyzing, cracking or refining a stagnate or flowing substance, comprising:
    a) a solid three-dimensional nanotube structure comprising heteroatom-doped carbon nanotubes, having a plurality of porous cavities, and
    b) an energy source, adapted to transfer electromagnetic radiation to the carbon nanostructure porous foam material at a predetermined frequency bandwidth,
    wherein the energy source comprises radio/microwave radiation,
    wherein the porous cavities of the solid three-dimensional carbon nanotube structures comprising heteroatom-doped carbon nanotubes are decorated with metals, metal oxides, or semiconductors, wherein the solid three-dimensional carbon nanostructured porous foam material nanotube structures comprising heteroatom-doped carbon nanotubes is micro-scaled.

8. A system for heating, evaporating, vaporizing, distilling, decomposing, pyrolyzing, cracking or refining a stagnate or flowing substance, comprising:
    a) a solid three-dimensional carbon nanostructured porous foam material nanotube structures comprising heteroatom-doped carbon nanotubes, having a plurality of porous cavities, and
    b) an energy source, adapted to transfer electromagnetic radiation to the carbon nanostructure porous foam material at a predetermined frequency bandwidth,
    wherein the material comprises carbon nanotubes, heteroatom-doped carbon nanotubes, graphene, heteroatom-doped graphene, graphitic microfibers, graphene oxide or combinations thereof,
    wherein the energy source comprises radio/microwave radiation, wherein the solid three-dimensional carbon nanostructured porous foam material comprising heteroatom-doped carbon nanotubes has a density less than 1 mg/cc.

9. A method for heating, evaporating, vaporizing, distilling, decomposing, pyrolyzing, cracking or refining a stagnate or flowing substance, comprising:
  a) providing a system comprising a solid three-dimensional carbon nanostructured porous foam material nanotube structures comprising heteroatom-doped carbon nanotubes, having a plurality of porous cavities, and an energy source, adapted to transfer electromagnetic radiation to the solid three-dimensional carbon nanostructured porous foam material nanotube structures comprising heteroatom-doped carbon nanotubes at a predetermined frequency bandwidth, wherein the energy source comprises radio/microwave radiation,
  b) at least partially filling the porous cavities of the porous solid three-dimensional carbon nanostructured porous foam material nanotube structures comprising heteroatom-doped carbon nanotubes with a stagnate or flowing substance, and
  c) using the energy source to heat the stagnate or flowing substance within the at least partially filled pores of the solid three-dimensional carbon nanostructured porous foam material nanotube structures comprising heteroatom-doped carbon nanotubes.

10. The method of claim 9, wherein the heating is sufficient to convert the stagnate or flowing substance into a heated, evaporated, vaporized, distilled, refined, pyrolyzed, cracked or decomposed product.

11. The method of claim 9, wherein the stagnate or flowing substance is selected from the group consisting of crude oil, tar, soot, water, steam, carbon dioxide, alcohols, natural gas, organics, alkanes, paraffins, cycloalkanes, naphthenes, asphaltene, hydrogen, hydrogen sulfide, coal, charcoal, coke, biomass, oil shale, organic waste, and aromatic hydrocarbon compounds.

12. The method of claim 9, wherein the transfer of electromagnetic radiation increases thermal activity in the solid three-dimensional carbon nanostructured porous foam material nanotube structures comprising heteroatom-doped carbon nanotubes, and the plurality of porous cavities is thereby increased in temperature.

13. The method of claim 9, wherein the pores in the porous cavities provide a relatively high surface area of contact with the stagnate or flowing substance, and stagnate or flowing substance is heated along the relatively high surface area of contact.

14. The method of claim 9, wherein the heating is microwave heating.

15. The method of claim 13, wherein the material being heated is selected from the group consisting of biomass, coal, oil shale, glycerol, and organic waste.

16. The method of claim 15, wherein the biomass comprises sewage sludge or biosolids.

17. The method of claim 9, wherein at least a portion of the stagnate or flowing substance being heated is gasified.

18. The method of claim 9, wherein the substance being heated is soil, and the soil is heated to remove impurities, thus providing remediated soil.

19. The method of claim 9, wherein the substance being heated comprises salt water, and the heating provides desalinated water.

20. The method of claim 9, wherein the substance being heated comprises methane and oxygen, and the heating involves dry reforming of the methane.

21. The method of claim 9, wherein the pores of the solid three-dimensional carbon nanostructured porous foam material nanotube structures comprising heteroatom-doped carbon nanotubes are decorated with metals, metal oxides, or semiconductors, or the three-dimensional carbon nanostructured porous foam material comprises nanotubes, and the nanotubes in the three-dimensional carbon nanostructured porous foam material are heteroatom doped.

* * * * *